US012625038B2

(12) United States Patent
Bomsztyk et al.

(10) Patent No.: US 12,625,038 B2
(45) Date of Patent: May 12, 2026

(54) TISSUE SAMPLE CORING SYSTEM

(71) Applicant: University of Washington, Seattle, WA (US)

(72) Inventors: Karol Bomsztyk, Seattle, WA (US); Stephen Scheuerman, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 1109 days.

(21) Appl. No.: 17/287,950

(22) PCT Filed: Oct. 24, 2019

(86) PCT No.: PCT/US2019/057835
§ 371 (c)(1),
(2) Date: Apr. 22, 2021

(87) PCT Pub. No.: WO2020/086829
PCT Pub. Date: Apr. 30, 2020

(65) Prior Publication Data
US 2021/0404915 A1      Dec. 30, 2021

Related U.S. Application Data

(60) Provisional application No. 62/751,187, filed on Oct. 26, 2018.

(51) Int. Cl.
*A61B 10/00* (2006.01)
*A61B 10/02* (2006.01)
(Continued)

(52) U.S. Cl.
CPC ........... *G01N 1/08* (2013.01); *A61B 10/0233* (2013.01); *A61B 10/0266* (2013.01); *A61B 2010/0208* (2013.01); *A61B 17/320758* (2013.01)

(58) Field of Classification Search
None
See application file for complete search history.

(56) References Cited

U.S. PATENT DOCUMENTS 5,148,729 A      9/1992  Krumdieck
5,156,160 A  *  10/1992  Bennett .............. A61B 10/0275
600/567

(Continued)

FOREIGN PATENT DOCUMENTS

CA          2882495          8/2015
WO      WO2010077657        7/2010

OTHER PUBLICATIONS

International Search Report and Written Opinion mailed Jan. 14, 2020 for International Application No. PCT/US19/57835, 7 pages.
(Continued)

*Primary Examiner* — Charles A Marmor, II
*Assistant Examiner* — Destiny J Cruickshank
(74) *Attorney, Agent, or Firm* — Perkins Coie LLP

(57) ABSTRACT

The present technology generally relates to a tissue sample coring system. Select embodiments of a tissue sample core extractor include a drill head, a drill bit, a tube, and a pump. The drill bit may have a hollow coring head configured to separate a core from a tissue sample and retain the core therein. The drill bit may include a central passageway fluidly coupling the hollow coring head to a port extending radially from the central passageway through the drill bit, where the tube is aligned with the port and movable to selectively abut the drill bit to create a fluid seal between the tube and the port such that the pump can cause a fluid to flow through the tube, pressurize the central passageway, and eject the core. The tissue sample core extractor may further include a trigger configured to move the tube and/or cycle the pump.

18 Claims, 4 Drawing Sheets

(51) Int. Cl.
  *G01N 1/08* (2006.01)
  *A61B 17/3207* (2006.01)

(56) References Cited

U.S. PATENT DOCUMENTS

| | | | |
|---|---|---|---|
| 6,022,324 | A | 2/2000 | Skinner |
| 6,053,877 | A | 4/2000 | Banik et al. |
| 6,090,103 | A | 7/2000 | Hakky et al. |
| 6,659,338 | B1 * | 12/2003 | Dittmann ................. G01N 1/04 |
| | | | 235/462.15 |
| 8,672,941 | B2 | 3/2014 | Bradica et al. |
| 2004/0097829 | A1 * | 5/2004 | McRury ............. A61B 17/3203 |
| | | | 600/564 |
| 2004/0191897 | A1 | 9/2004 | Muschler |
| 2005/0059905 | A1 | 3/2005 | Boock et al. |
| 2006/0047272 | A1 * | 3/2006 | McPherson ........ A61B 17/1626 |
| | | | 606/1 |
| 2006/0074345 | A1 | 4/2006 | Hibner |
| 2008/0281225 | A1 | 11/2008 | Spero et al. |
| 2010/0184127 | A1 | 7/2010 | Williamson, IV et al. |
| 2010/0190170 | A1 | 7/2010 | Yu et al. |
| 2012/0322070 | A1 | 12/2012 | Nevo |
| 2014/0039343 | A1 * | 2/2014 | Mescher ................ A61B 90/98 |
| | | | 600/562 |
| 2014/0326083 | A1 | 11/2014 | Basque et al. |
| 2015/0158027 | A1 | 6/2015 | Fleming et al. |
| 2015/0238171 | A1 * | 8/2015 | Shabaz .............. A61B 10/0266 |
| | | | 600/567 |
| 2016/0116380 | A1 * | 4/2016 | Bladen ................. A01K 11/002 |
| | | | 435/309.1 |
| 2016/0249888 | A1 | 9/2016 | Gardner et al. |
| 2016/0341712 | A1 | 11/2016 | Agar |
| 2017/0055966 | A1 | 3/2017 | Vetter et al. |

OTHER PUBLICATIONS

Aldridge, S., Watt, S., Quail, M.A., Rayner, T., Lukk, M., Bimson, M.F., Gaffney, D. and Odom, D.T. (2013) AHT-ChIP-seq: a completely automated robotic protocol for high-throughput chromatin immunoprecipitation. *Genome Biol.*, 14, R124.
Barski, A. et al., (2007) High-resolution profiling of histone methylations in the human genome. Cell, 129, 823-837.
Bernstein, B.E., Birney, E., Dunham,I., Green, E.D., Gunter,C. and Snyder, M. (2012) An integrated encyclopedia of DNA elements in the human genome. Nature, 489, 57-74.
Birnbaum, R.Y., et al., (2012) Coding exons function as tissue-specific enhancers of nearby genes. Genome Res., 22, 1059-1068.
Blecher-Gonen, R., Barnett-Itzhaki, Z., Jaitin, D., Amann-Zalcenstein,D., Lara-Astiaso, D. and Amit, I. (2013) High-throughput chromatin immunoprecipitation for genome-wide mapping of in vivo protein-DNA interactions and epigenomic states. Nat. Protoc., 8, 539-554.
Bomsztyk, K. et al., (2015) Experimental acute lung injury induces multi-organ epigenetic modifications in key angiogenic genes implicated in sepsis-associated endothelial dysfunction. Crit. Care, 19, 225.
Bomsztyk, K., Flanagin, S., Mar, D., Mikula, M., Johnson, A., Zager, R. and Denisenko, O. (2013) Synchronous recruitment of epigenetic modifiers to endotoxin synergistically activated Tnf-alpha gene in acute kidney injury. *PLoS One*, 8, e70322.
Brind'Amour, J., Liu, S., Hudson, M., Chen, C., Karimi, M.M. and Lorincz, M.C. (2015) An ultra-low-input native ChIP-seq protocol for genome-wide profiling of rare cell populations. *Nat. Commun.*, 6, 6033.
Chen, Y., Blair, K. and Smith, A. (2013) Robust Self-Renewal of rat embryonic stem cells requires fine-tuning of glycogen synthase Kinase-3 inhibition. Stem Cell Rep., 1, 209-217.
Ernst, J. et al. (2011) Mapping and analysis of chromatin state dynamics in nine human cell types. Nature, 473, 43-49.

Flanagin, S., Nelson, J.D., Castner, D.G., Denisenko, O. and Bomsztyk, K. (2008) Microplate-based chromatin immunoprecipitation method, Matrix ChIP: a platform to study signaling of complex genomic events. *Nucleic Acids Res.*, 36, e17.
Freberg, C.T., Dahl, J.A., Timoskainen, S. and Collas, P. (2007) Epigenetic reprogramming of OCT4 and NANOG regulatory regions by embryonal carcinoma cell extract. Mol. Biol. Cell, 18, 1543-1553.
Garber, M., Yosef, N., Goren, A., Raychowdhury, R., Thielke, A., Guttman, M., Robinson, J., Minie, B., Chevrier,N., Itzhaki, Z. et al. (2012) A high-throughput chromatin immunoprecipitation approach reveals principles of dynamic gene regulation in mammals. *Mol. Cell*, 47, 810-822.
Gasper, W.C. et al., (2014) Fully automated high-throughput chromatin immunoprecipitation for ChIP-seq: identifying ChIP-quality p300 monoclonal antibodies. Sci. Rep., 4, 5152.
Hall, T. and Cain, C. (2006) A low cost compact 512 channel therapeutic ultrasound system for transcutaneous ultrasound surgery. In: Clement, GT, McDannold, NJ and Hynynen, K (eds). AIP Conference Proceedings. AIP, NY, vol. 829, pp. 445-449.
Heintzman, N.D., Stuart, R.K., Hon, G., Fu, Y., Ching, C.W., Hawkins, R.D., Barrera, L.O., Van Calcar, S., Qu, C., Ching, K.A. et al. (2007) Distinct and predictive chromatin signatures of transcriptional promoters and enhancers in the human genome. Nat. Genet., 39, 311-318.
Hou, P. et al., (2013) Pluripotent stem cells induced from mouse somatic cells by small-molecule compounds. Science, 341, 651-654.
Huang, W. et al., (2010) Network-based comparison of temporal gene expression patterns. Bioinformatics, 26, 2944-2951.
Huebert, D.J., Kamal, M., O'Donovan, A. and Bernstein, B.E. (2006) Genome-wide analysis of histone modifications by ChIP-on-chip. *Methods*, 40, 365-369.
Kuo, M.H. and Allis, C.D. (1999) In vivo cross-linking and immunoprecipitation for studying dynamic Protein:DNA associations in a chromatin environment. Methods, 19, 425-433.
Landt, S.G. et al., (2012) ChIP-seq guidelines and practices of the ENCODE and modENCODE consortia. Genome Res., 22, 1813-1831.
Li, H. and Durbin, R. (2009) Fast and accurate short read alignment with Burrows-Wheeler transform. Bioinformatics, 25, 1754-1760.
Mar, D. et al., (2015) Heterogeneity of epigenetic changes at ischemia/reperfusion- and endotoxin-induced acute kidney injury genes. Kidney Int., 88, 734-744.
Marks, H. et al., (2012) The transcriptional and epigenomic foundations of ground state pluripotency. Cell, 149, 590-604.
Mathieu, J. et al., (2019) Folliculin regulates mTORC1/2 and WNT pathways in early human pluripotency. Nat. Commun., 10, 632.
Meyer, C.A. and Liu, X.S. (2014) Identifying and mitigating bias in next-generation sequencing methods for chromatin biology. *Nat. Rev. Genet.*, 15, 709-721.
Mikula, M. et al., (2016) Genome-wide co-localization of active EGFR and downstream ERK pathway kinases mirrors mitogen-inducible RNA polymerase 2 genomic occupancy. Nucleic Acids Res., 44, 10150-10164.
Mikula, M. and Bomsztyk, K. (2011) Direct recruitment of ERK cascade components to inducible genes is regulated by the heterogeneous nuclear ribonucleoprotein (HnRNP) K. J. Biol. Chem., 286, 9763-9775.
Morris, D.P., et al., (2015) Temporal dissection of rate limiting transcriptional events using Pol II ChIP and RNA analysis of adrenergic stress gene activation. PLoS One, 10, e0134442.
Nelson, J.D., Leboeuf, R.C. and Bomsztyk, K. (2011) Direct recruitment of insulin receptor and ERK signaling cascade to insulin-inducible gene loci. Diabetes, 60, 127-137.
O'Neill, L.P. and Turner, B.M. (1996) Immunoprecipitation of chromatin. *Methods Enzymol.*, 274, 189-197.
Orlando, V., Strutt, H. and Paro, R. (1997) Analysis of chromatin structure by in vivo formaldehyde cross-linking. *Methods*, 11, 205-214.
Ostrowski, J. et al., (2001) Insulin alters heterogeneous ribonucleoprotein K protein binding to DNA and RNA. Proc. Natl. Aca. Sci. U.S.A., 98, 9044-9049.

(56) References Cited

OTHER PUBLICATIONS

Quinlan, A.R. and Hall, I.M. (2010) BEDTools: a flexible suite of utilities for comparing genomic features. Bioinformatics, 26, 841-842.

Ramirez, F. et al., (2014) deepTools: a flexible platform for exploring deep-sequencing data. Nucleic Acids Res., 42, W187-W191.

Schmidl, C., Rendeiro, A.F., Sheffield, N.C. and Bock, C. (2015) ChIPmentation: fast, robust, low-input ChIP-seq for histones and transcription factors. *Nat Methods*, 12, 963-965.

Schoppee Bortz, P.D. and Wamhoff, B.R. (2011) Chromatin immunoprecipitation (ChIP): revisiting the efficacy of sample preparation, sonication, quantification of sheared DNA, and analysis via PCR. *PLoS One*, 6, e26015.

Sharifian, R. et al., (2018) Distinct patterns of transcriptional and epigenetic alterations characterize acute and chronic kidney injury. Sci. Rep., 8, 17870.

Skene, P.J. and Henikoff, S. (2015) A simple method for generating high-resolution maps of genome-wide protein binding. *Elife*, 4, e09225.

Skene, P.J., Henikoff, J.G. and Henikoff, S. (2018) Targeted in situ genome-wide profiling with high efficiency for low cell numbers. *Nat. Protoc.*, 13, 1006-1019.

Solomon, M.J. and Varshavsky, A. (1985) Formaldehyde-mediated DNA-protein crosslinking: a probe for in vivo chromatin structures. *Proc. Natl. Acad. Sci. U.S.A.*, 82, 6470-6474.

Sperber, H., et al., (2015) The metabolome regulates the epigenetic landscape during naive-to-primed human embryonic stem cell transition. Nat. Cell Biol., 17, 1523-1535.

Ware, C.B. et al., (2014) Derivation of naive human embryonic stem cells. Proc.Natl. Acad. Sci. U.S.A., 111, 4484-4489.

Yu, J., Feng, Q., Ruan, Y., Komers, R., Kiviat, N. and Bomsztyk, K. (2011) Microplate-based platform for combined chromatin and DNA methylation immunoprecipitation assays. *BMC Mol. Biol.*, 12, 49.

Zarnegar, M.A., Reinitz, F., Newman, A.M. and Clarke, M.F. (2017) Targeted chromatin ligation, a robust epigenetic profiling technique for small cell numbers. *Nucleic Acids Res.*, 45, e153.

Zhang, Y., Liu, T., Meyer, C.A., Eeckhoute, J., Johnson, D.S., Bernstein, B.E., Nusbaum, C., Myers, R.M., Brown, M., Li, W. et al. (2008) Model-based analysis of ChIP-Seq (MACS). Genome Biol., 9, R137.

* cited by examiner

TISSUE SAMPLE CORING SYSTEM

CROSS-REFERENCE TO RELATED APPLICATION(S)

The present application is a National Phase of International Patent Application No. PCT/US19/57835, titled "TISSUE SAMPLE CORING SYSTEM," filed Oct. 24, 2019. which claims priority to U.S. Provisional Patent Application No. 62/751,187, titled "TISSUE CORING MULTISAMPLER DEVICE," filed Oct. 26, 2018, the disclosure of which are hereby incorporated by reference in their entireties.

STATEMENT OF FEDERALLY SPONSORED RESEARCH AND DEVELOPMENT

This invention was made with government support under Grant Nos. ROL DK103849 and R21 GM111439 and R33 CA191135 and R42 HG01085S and R44 GM122097 awarded by the National Institutes of Health. The government has certain rights in the invention.

TECHNICAL FIELD

The present technology generally relates to systems and methods for obtaining tissue samples by coring cryogenic tissues.

BACKGROUND

Histological and molecular intra-tissue heterogeneity is present in virtually every disease, including cancer and organ injury. This heterogeneity is thought to account for many therapeutic failures (particularly in cancer), and is shifting the paradigm that multiple, as opposed to single, biopsies are needed to optimize personalized medical care. There are powerful high throughput pre-analytical sample preparation and analytical platforms to study intracellular processes and their alterations in tissues, including molecular intratissue heterogeneity in cancer and organ injury. Freezing or paraffin embedding of formalin fixed tissues (FFPE) is a common way to preserve and store samples for analysis (e.g. surgical specimens for pathologist evaluation).

Advances in high throughput (HT) sample preparation and analytical technologies are providing opportunities to study intra-tissue heterogeneity, leading to discoveries of disease biomarkers. Such HT platforms that analyze multiple sections within a tissue have not been fully utilized due to relatively slow and tedious sampling of frozen and FFPE tissues, currently obtained by using a scalpel, microtome, laser capture microdissection, or by crushing frozen samples with hammer-like tools. Tissue biopsies are among the most common medical procedures used to establish diagnosis. Historically, tissue biopsies were primarily used for histology. More recently, with increasing understanding of molecular basis of disease, tissue samples are being used in personalized medicine where treatments are based on discoveries of molecular biomarkers.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

A. Overview

Figure 1:
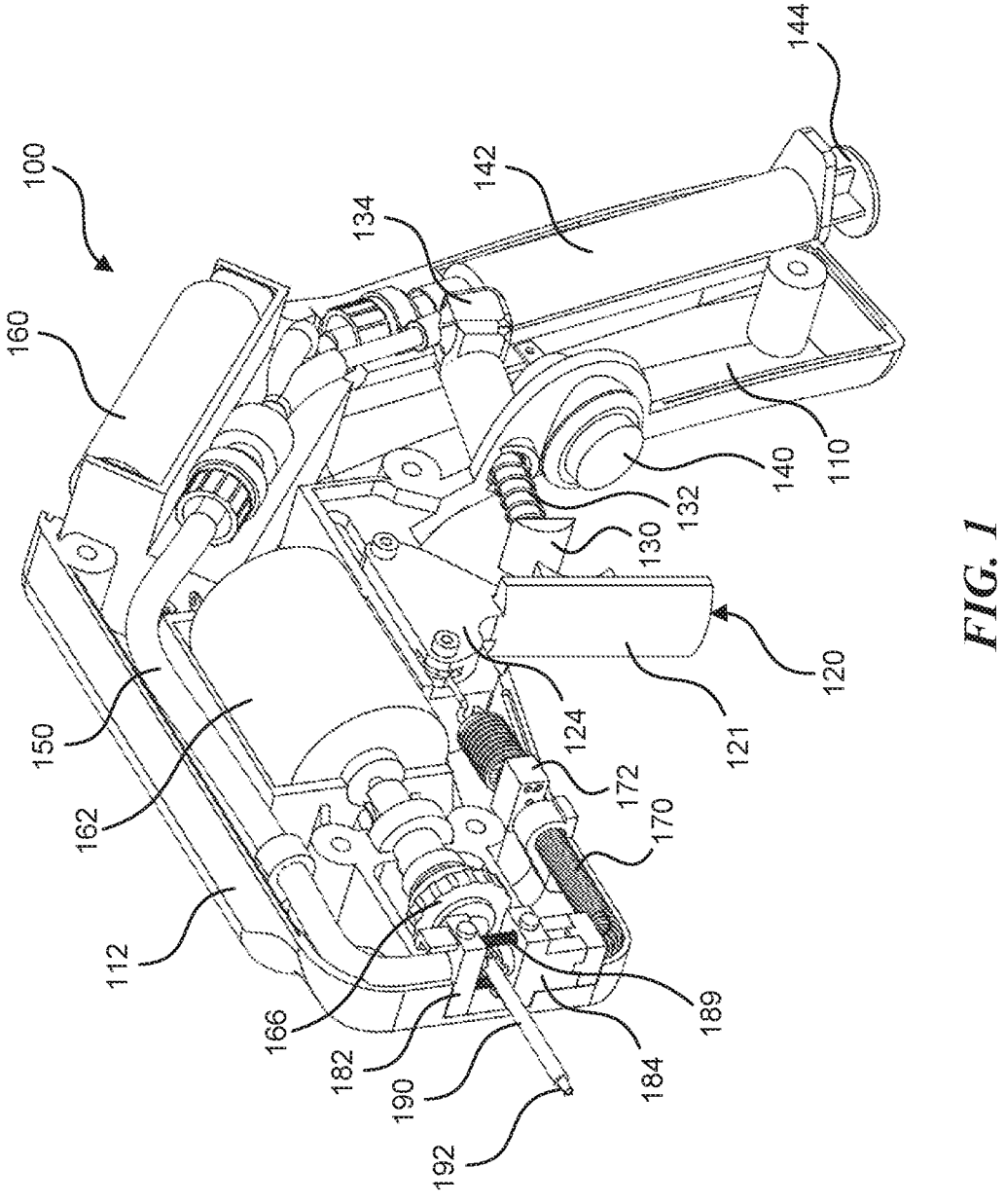
FIG. 1 is a perspective view of a tissue sample coring device configured in accordance with an embodiment of the present technology.

The present technology is directed to a tissue sample coring system having a tissue sample core extractor. The tissue sample coring device is configured to remove a substantially cylindrical portion of a tissue sample (a "core") from a cryogenically frozen block of fresh tissue for molecular and/or histology testing, among other uses. Under certain testing protocols, it is necessary to maintain the cores in a frozen state to preserve the normal and/or diseased cells, preventing the cells from changing state during preparation, transportation, and/or storage of the samples.

To obtain a core, a motor of the tissue sample core extractor ("coring tool") is energized to rotate a miniature coring drill bit configured to separate the core from the frozen tissue block in a cryogenic container. The coring drill bit can have any suitable diameter and may include a shoulder configured to provide a physical obstruction for the coring drill bit at a desired depth into the block. The rotating coring drill bit is driven into the frozen tissue at a desired depth and/or until the tissue reaches the shoulder, filling the bore of the coring drill bit with the frozen tissue core. The coring drill bit is removed from the block to extract the core and the motor is stopped.

After the coring drill bit is removed from the tissue block, a dual-stage trigger is actuated through a first stage to clamp tubing around holes in the shank of the coring drill bit. Before actuation of the trigger through a second stage, the coring tool is primed or flushed with buffered fluid, e.g., a phosphate buffer saline (PBF). As the trigger is actuated through the second stage, a jet of PBF flows through the holes to apply pressure to eject the extracted core from the coring drill bit. In other embodiments, the trigger can eject the core with a single-stage actuation, e.g., in embodiments where the tubing is positioned to continually surround the holes of the shank of the coring drill bit. The core may be ejected for testing.

Coring tools configured in accordance with the present technology may be configured to provide cores for studies involving high throughput analytical applications in multiple organs and tumors (e.g., genomics, epigenetics, transcriptomics, proteomics, metabolomics, etc.). Such studies generally identify disease tissue biomarkers for personalized medicine. In this regard, embodiments of the present technology provide a multisampling-capable coring tool that can be used in clinical settings, e.g., in resected tumors where intratumor genomic and epigenetic heterogeneity is expected to guide personalized treatment.

The coring tools described herein are configured to extract cores from frozen tissues in a specified size, e.g., cores from 1-2 mm long and about 1 mm in diameter. However, other lengths and diameters are within the scope of the present technology. Among other tissues, the coring tool is config- ured to extract cores from frozen brain, heart, kidney, liver, lung, and muscle tissue. Cores extracted from organs can be processed in a high throughput (HT) pre-analytical sample preparation instrument to shear chromatin and isolate ribo- nucleic acid (RNA), deoxyribonucleic acid (DNA), and protein.

B. Selected Embodiments of a Tissue Sample Coring Device

Embodiments of the tissue sample coring device are configured to extract and eject a core tissue specimen in the form of a core, and generally include a coring drill bit rotatable by a motor, a trigger assembly 120 having a fluid pump, and a fluid source. In some embodiments, the rotation of the coring drill is initiated by a switch (e.g., a button) on the drill body or integrated with the trigger assembly 120. In embodiments having dual-stage triggers, pulling or actuat- ing the trigger assembly 120 through a first stage engages a tube clamping mechanism, which creates a seal around a portion of the coring drill where fluid may be introduced to an anterior area of the core portion of the drill bit behind the core. When the trigger is further actuated through the second stage, the trigger depresses a plunger which pumps fluid into the anterior area of the coring drill bit. The fluid pressure is applied to the core to eject the core from the coring drill bit. In other embodiments, the trigger includes an additional stage or button to initiate the rotation of the coring drill. In further embodiments, the tube clamping mechanism may be omitted such that the tube provides a continuous pathway for fluid to flow into the anterior area of the drill bit.

Figure 2:
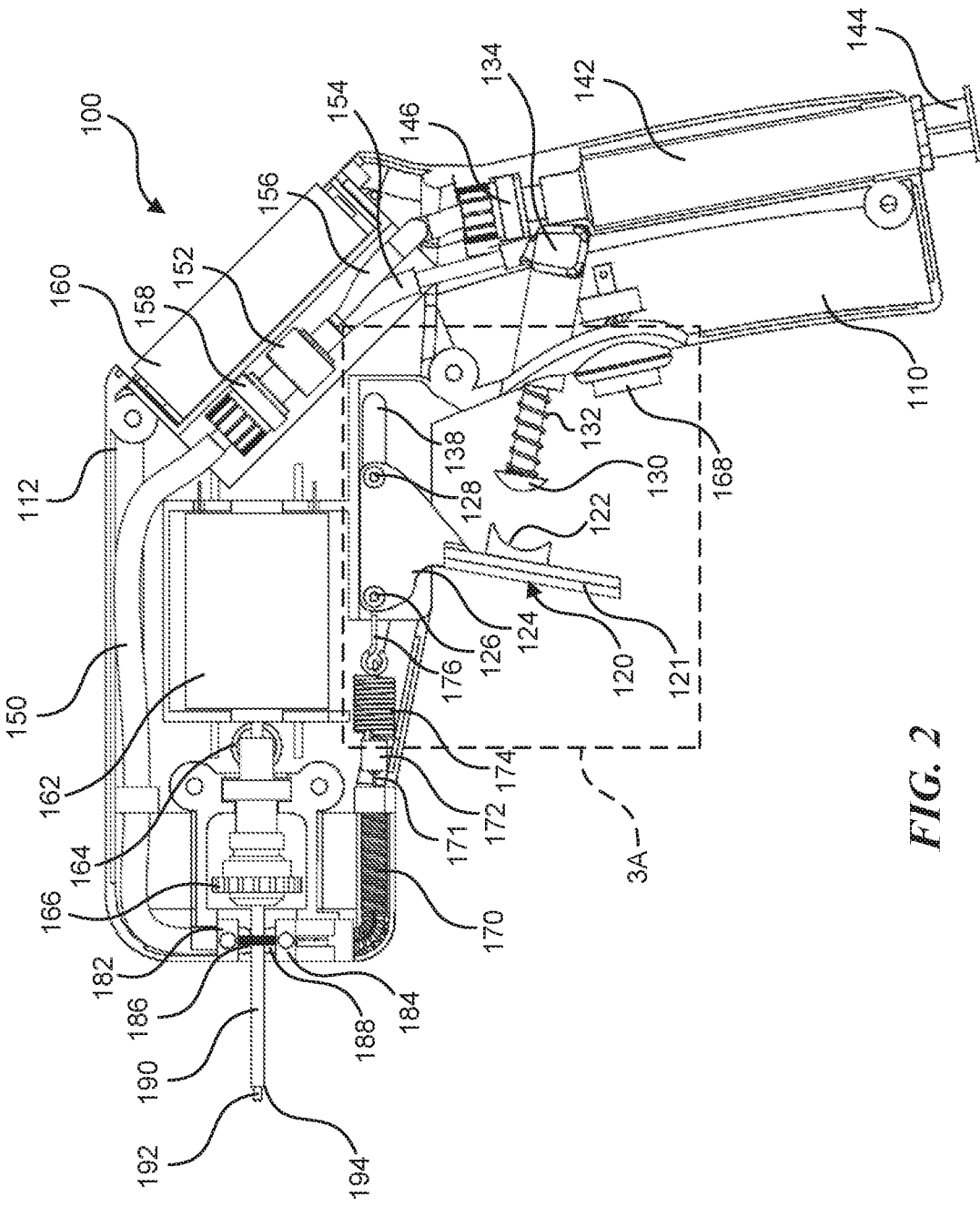
FIG. 2 is a right side elevation view of the tissue sample coring device of FIG. 1.

FIG. 1 is a perspective view and FIG. 2 is a right side elevation view of a tissue sample coring tool or coring device 100 configured in accordance with an embodiment of the present technology. Referring to FIGS. 1 and 2 together, the coring tool 100 generally includes an outer body 112 to protect and encase the components of the coring tool 100. The outer body 112 may include two or more portions (e.g., two halves in a clamshell-type configuration) to surround, position, and protect the components of the coring tool 100, and to provide surfaces to ergonomically interact with the user, such as a handle 110 where a user may grasp the coring tool 100 to position, operate, and manipulate the coring tool 100. For purposes of illustration, the coring tool 100 is shown partially disassembled in FIGS. 1 and 2 with a portion of the outer body 112 removed to expose the internal components. The outer body 112 may be formed from plastic (e.g., acrylonitrile butadiene styrene (ABS)), metal, or any other suitable material to encase the components of the coring tool 100.

The coring tool 100 has various components configured for user interface during operation of the coring tool 100 to extract a core (not shown). For example, the coring tool 100 may include a trigger assembly 120 having a trigger plate 121 and an actuator 130. The trigger plate 121 projects from and is slidably associated with the outer body 112 and is configured to travel between various positions based on manipulation by the user, e.g., by applying a rearward pressure to a surface of the trigger plate 121 with one or more fingers. As best seen in FIG. 2, the trigger plate 121 may include an arcuate engaging surface 122 configured to interface with a complementary arcuate surface of an actua- tor 130 projecting from the handle 110. The arcuate engag- ing surface 122 maintains contact with the actuator 130 during translation and rotation of the trigger plate 121 as the trigger assembly 120 is actuated through the stages, which will be described in greater detail below.

Referring back to FIGS. 1 and 2 together, the actuator 130 may include a spring 132 to provide a restorative force against the actuator 130 to return the actuator 130 to an initial position (e.g., the illustrated position in FIGS. 1 and 2), where the actuator 130 is ready for subsequent actuation by the trigger plate 121. The actuator 130 may be configured to cycle a pump 134 to pressurize and flow PBF through the coring tool 100 to eject the core after extraction. The PBF may be stored internal to the outer body 112, such as in a container 142 generally having a cylinder and plunger configuration (e.g., a syringe). To prime the coring tool 100, the container 142 may include a plunger 144 configured to transfer the PBF from the container 142 through a first one-way check valve 146 and into a chamber 152 (see FIG. 2) such that the PBF can be further pressurized by the pump 134 for delivery to the core. In some embodiments, the first one-way check valve 146 prevents backflow of the PBF into the container 142. The actuator 130 may be a polytetrafluo- roethylene (PTFE) rod or any other suitable material pro- viding a sufficiently low friction coefficient, corrosion resis- tance, and a water-tight seal, among other features.

The pump 134 and the container 142 are fluidly coupled to the chamber 152 where pressurization from the pump 134 causes the PBF to flow through the coring tool 100. In particular, the pump 134 is fluidly coupled to the chamber 152 through a first duct 154 and the container 142 is fluidly coupled to the chamber 152 through a second duct 156. As the pump 134 is cycled by the trigger plate 121 through the actuator 130, fluid or air from the pump 134 is routed to the chamber 152, pressurizing the chamber 152. The pressur- ization of the chamber 152 causes PBF to flow through a second one-way check valve 158 and into a primary fluid duct 150. When pressure on the actuator 130 is released, the pump 134 or a void in the chamber 152 may cause a vacuum to pull additional PBF from the container 142 through the first one-way check valve 146 for the next trigger cycle.

During operation, the coring tool 100 extracts a core using a drill assembly, which generally includes a drill head 166 configured to removably couple or clamp around a drill bit 190 positioned therein. The motor 162 is configured to rotate the drill assembly. The drill head 166 may include any suitable chuck or collet configuration for clamping the drill bit 190, such as a chuck rotationally tightened with a chuck key, a hand-tightened chuck or collet, etc. In embodiments of the drill head 166 having a rotationally tightened chuck, a rotation lock button 164 may be positioned on the coring tool 100 to stop the free rotation of the drill head 166, such that the chuck can be loosened to release the drill bit 190 or tightened to clamp around the drill bit 190. In the illustrated embodiment, the drill head 166 is positioned inset from the outer body 112 such that the rotating portion of the drill head 166 is not protruding from the outer body 112 but can still be accessed by the user to manipulate the chuck. Such configurations are expected to be beneficial in a lab envi- ronment, where work clothing and other items may become stuck within a protruding rotating drill head. In other embodiments, however, the drill head 166 may be at least partially protruding from the outer body 112.

As best seen in FIG. 2, the drill assembly may further include a motor 162 driven by a power supply 160 electri- cally coupled to the motor 162 (electrical wires are not shown for clarity). The power supply 160 may be an onboard battery, such as a battery 160 shown in FIGS. 1 and 2, or can be an external power source or external battery to provide power to the motor 162. The power supply 160 may be switched by an electrical switch 168 located on the outer body 112 of the coring tool 100. In some embodiments, the electrical switch 168 is momentary, where pressure must be maintained on the electrical switch 168 by the user to continue power supply to the motor 162. In other embodiments, the electrical switch 168 can be a toggle switch or any other suitable switch to selectively couple the power supply 160 and the motor 162. In further embodiments, the electrical switch 168 is integrated into the trigger plate 121, or external to the coring tool 100, such as a foot-actuated switch, etc.

Figure 3A:
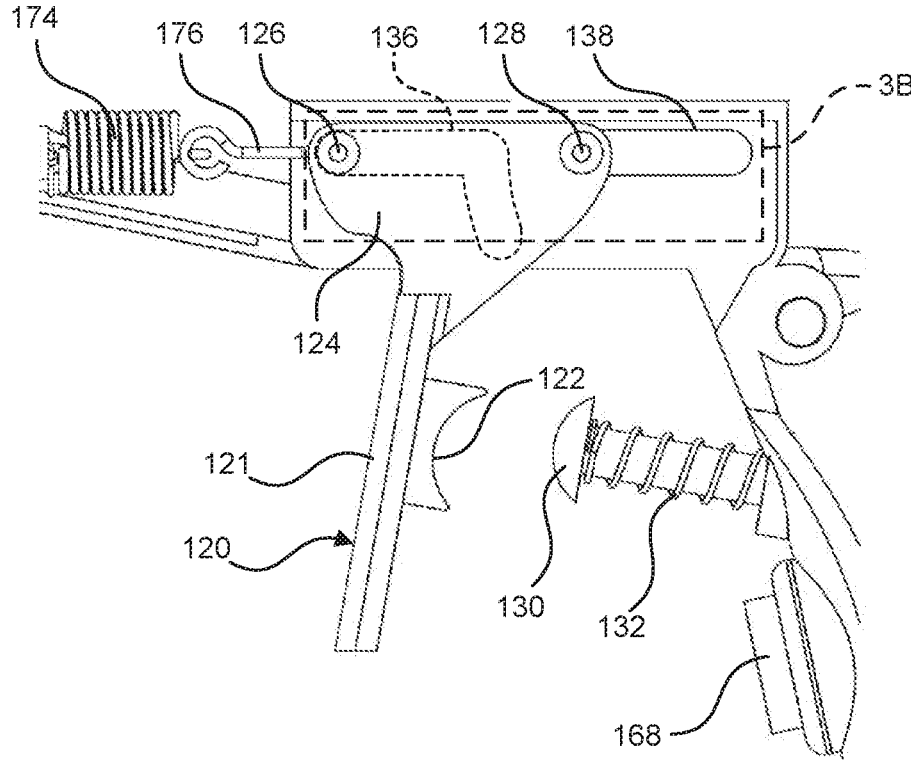
FIG. 3A is an enlarged detail view of the trigger area of the tissue sample coring device of FIG. 1, taken at the boundary shown in FIG. 2.
Figure 3B:
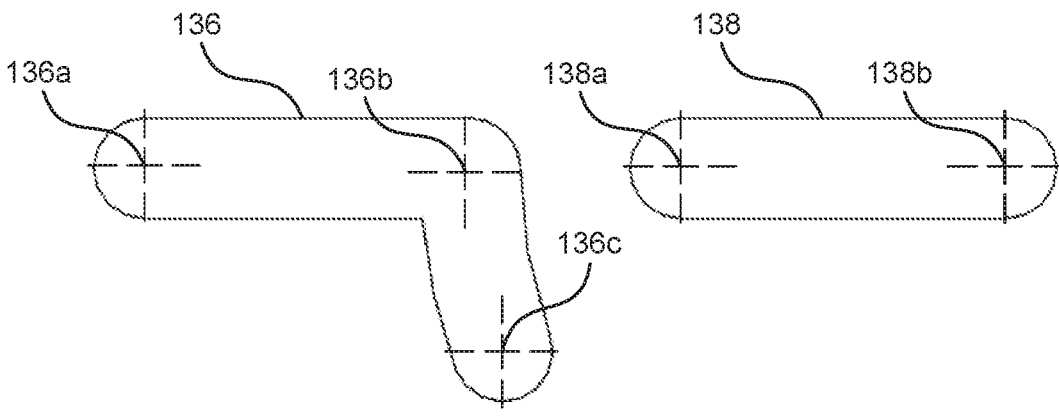
FIG. 3B is an enlarged detail view of the trigger slots of the tissue sample coring device of FIG. 1, taken at the boundary shown in FIG. 3A with the trigger body hidden.

As noted previously, the coring tool 100 includes the dual stage trigger assembly 120. FIG. 3A, for example, is an enlarged detail view of the trigger assembly 120 region of the coring tool 100 taken along the boundary shown in FIG. 2, and FIG. 3B is an enlarged detail view taken at the boundary shown in FIG. 3A (and with the trigger body 124 hidden). Referring first to FIG. 3A, the trigger plate 121 protrudes from a trigger body 124 that is slidingly and rotatably associated with the outer body 112. The trigger body 124 includes a first pin 126 and a second pin 128 configured to interface with first and second slots 136 and 138, respectively, positioned within the outer body 112, or positioned on a separate plate attached to the outer body 112. Referring to FIGS. 3A and 3B together, the first slot 136 has a linear slot portion between a first position 136a and a second position 136b, along which the first pin 126 travels during the first stage of actuation of the trigger assembly 120, e.g., a linear pull of the trigger plate 121. The first and second pins 126 and 128 may include bearings to decrease friction during travel through the first and second slots 136 and 138, respectively.

The second slot 138 is a linear slot having a first position 138a and a second position 138b between which the second pin 128 travels during the first stage of actuation of the trigger assembly 120. The slot profile at the first positions 136a and 138a and the second positions 136b and 138b may be contoured to correspond to the shape of the first pin 126, which is shown in a circular configuration. In other embodiments, the slots 136 and 138 and the pins 126 and 128 are any suitable shape. When the trigger assembly 120 is in its initial position, the first and second pins 126 and 128 are aligned with the first positions 136a and 138a, respectively, and as the trigger assembly 120 is actuated through the first stage, the first and second pins 126 and 128 travel along the linear portions of the first and second slots 136 and 138 until the first and second pins 126 and 128 reach the second positions 136b and 138b, respectively.

At the end of the first stage of the trigger assembly 120, the first and second pins 126 and 128 are located in the second positions 136b and 138b, respectively, where rearward travel of the trigger assembly 120 is stopped. In this regard, the end of at least the second slot 138 at the second position 138b abuts the second pin 128 to stop the trigger assembly 120 from further linear movement. As the trigger plate 121 is further actuated from this position, the second stage of the trigger assembly 120 is initiated. To guide the trigger plate 121 along the second stage, the first slot 136 additionally includes an arcuate portion between the second position 136b and a third position 136c, along which the first pin 126 travels during the second stage of actuation of the trigger assembly 120. The arcuate portion of the first slot 136 is generally shaped as a circumferential path from the second position 136b to the third position 136c about a pivot point of the second position 138b of the second slot 138. During actuation through the second stage of the trigger assembly 120, the first pin 126 travels along the arcuate portion of the first slot 136 from the second position 136b to the third position 136c, rotating about the second pin 128 in the second position 138b of the second slot 138.

During actuation of the trigger assembly 120 near the end of the first stage, or the beginning of the second stage, the arcuate engagement surface 122 contacts the complementary arcuate surface of the actuator 130 and begins to depress the actuator 130 to cycle the pump 134. As the trigger assembly 120 is actuated further through the second stage, the actuator 130 is fully depressed and cycles the pump 134 to flow PBF through the primary fluid duct 150, positioned radially outward from the drill bit 190, and eject the core. Upon release of the trigger assembly 120, a spring 174, coupled to the trigger body 124 through a link 176, applies a force to reverse the travel of the first and second pins 126 and 128 within the first and second slots 136 and 138, respectively, first rotating the trigger assembly 120 such that the first pin 126 travels from the third position 136c to the second position 136b, then translating the trigger assembly 120 such that the first and second pins 126 and 128 travel from the second positions 136b and 138b, to the first positions 136a and 138a, respectively, where trigger assembly 120 is ready for further actuations.

Returning to FIGS. 1 and 2, the linear translation during actuation through the first stage of the trigger assembly 120 pulls on a cable 171 attached to the trigger body 124 through a distribution block 172, the spring 174, and the link 176. One or more cables 171 may be coupled to the trigger body 124 through the distribution block 172, which is also configured to adjust the length of the cable 171. The cable 171 is routed through a protective tube 170, which allows the routing path of the cable 171 to change direction, such as a directional change of about 90°, as shown most clearly in FIG. 2. The cable 171 may be any suitable material, e.g., nylon cord, metal wire, etc.

The end of the cable 171 opposite the distribution block 172 is coupled to an upper jaw 182 and a lower jaw 184 positioned on either side of (e.g., diametrically opposed) and adjacent to the drill bit 190 near the drill head 166. The primary fluid duct 150 has a proximal end 186 extending through and carried by the upper jaw 182 toward the drill bit 190. The lower jaw 184 may also have a blind duct portion 188 extending through and carried by the lower jaw 184 toward the drill bit 190.

During actuation through the first stage of the trigger assembly 120, the cable 171 is pulled in a direction toward the trigger body 124, which draws the upper jaw 182 and lower jaw 184 together around the drill bit 190, such that the movable proximal end 186 of the primary fluid duct 150 and the movable duct portion 188, which are initially spaced apart from the drill bit 190, clamp together around the drill bit 190 to create a fluid-tight seal. Each of the proximal end 186 and duct portion 188 may be shaped to correspond to the shape of the drill bit 190. In some embodiments, the proximal end 186 and the duct portion 188 are comprised of any suitable flexible, noncorrosive tubing configured to create the fluid-tight seal, such as silicone tubing. The seal is created prior to the actuation of the trigger assembly 120 through the second stage where the PBF is pumped by the pump 134 through the primary fluid duct 150 to the drill bit 190. During actuation of the trigger assembly 120 through the second stage, the spring 174 elongates, which allows the trigger plate 121 to continue to travel through the second stage without further movement of the cable 171 or upper and lower jaws 182 and 184.

Features of the drill bit 190 will now be described in detail with reference to FIG. 4. The drill bit 190 is configured to rotate (while clamped by the drill head 166—FIG. 2) and cut the core from the frozen tissue block (not shown). The drill bit 190 may include a hollow coring head 192, a shoulder 194, a central passageway 196, and one or more fluid ports 198 extending radially from the central passageway 196 through the drill bit 190. The coring head 192 may be serrated and/or include one or more teeth 193 to cut the material around the core in the frozen tissue block and retain the core therein. As noted above, the shoulder 194 is configured to provide a physical obstruction for the drill bit 190 at a desired depth into the frozen tissue block to prevent the coring head 192 from entering the tissue sample to a depth farther than the depth of the shoulder 194.

Figure 4:
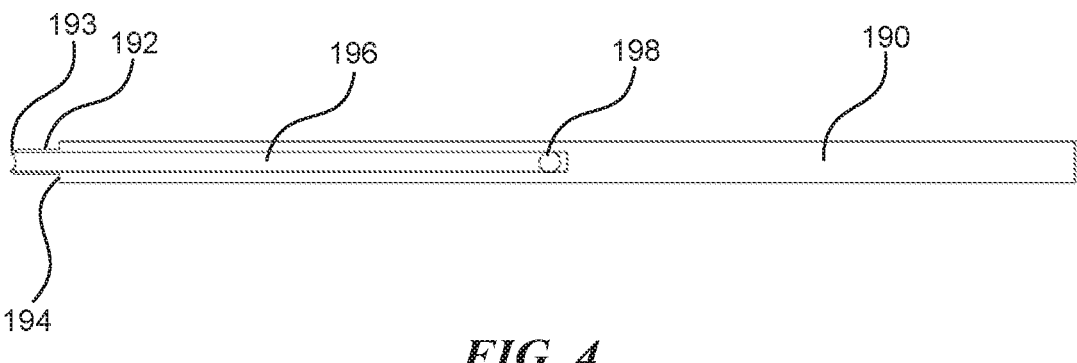
FIG. 4 is an enlarged detail view of the drill bit of the tissue sample coring device of FIG. 1.

Referring to FIGS. 1, 2, and 4 together, when the drill bit 190 is positioned in the drill head 166, the fluid ports 198 are generally aligned with the proximal end 186 of the primary fluid duct 150 and the duct portion 188 between the upper and lower jaws 182 and 184. In some embodiments, the drill bit 190 is comprised of any suitable metal, such as stainless steel, titanium, tungsten, etc., to provide durability and corrosion resistance. As the fluid-tight seal is created around the drill bit 190 near the end of the first stage of trigger actuation, a fluid connection is made between the primary fluid duct 150 (FIG. 2) and the central passageway 196 of the drill bit 190 through the fluid ports 198. The fluid connection between the primary fluid duct 150 and the central passageway 196 is maintained during the actuation of the trigger assembly 120 through the second stage, where the PBF flows through the proximal end 186 of the primary fluid duct 150, through the fluid ports 198, and into the central passageway 196. The duct portion 188 is configured with a blind to prevent PBF flow from exiting a fluid port 198. The central passageway 196 is configured to direct the PBF to a distal side of the core positioned within the central passageway 196 at the coring head 192. The pressure of the PBF created by the pump 134 applies a force to the distal side of the core, causing the core to eject from the drill bit 190.

Upon release of the trigger assembly 120, the flow of PBF to the drill bit 190 is stopped and the upper and lower jaws 182 and 184 retract to pull the proximal end 186 and the duct portion 188 away from the drill bit 190. The retraction of the upper and lower jaws 182 and 184 may be assisted by one or more springs 189 (FIG. 1). As noted above, in other embodiments, the upper and lower jaws 182 and 184 may be stationary such that the tubes provide a continuous pathway for fluid to flow into the anterior area of the drill bit 190. In such embodiments, the proximal end 186 and the duct portion 188 are configured to withstand the friction created during the spinning of the drill bit 190.

In other embodiments, the coring tool 100 uses a gas in place of the PBF to eject the core. In these embodiments, the actuator 130 may be configured to pressurize the gas, similarly to the pumping system described above, or the actuator 130 may be configured to throttle a pressurized gas from a supply, such as a compressed gas source. Similar components of the coring tool 100 may be adapted to be used with gas, such as the size, shape, and/or material of the ducts, check valves, chamber, upper and lower jaws, etc. In further embodiments, additional features may be added to the coring tool 100, such as a barcode reader (not shown) configured to receive identifying information regarding the tissue sample to aid the user in extraction of the core from frozen tissue sample blocks.

8

C. Additional Examples

Several aspects of the present technology are set forth in the following examples.

1. A tissue sample core extractor, comprising:
   a drill head configured to be rotated by a motor;
   a drill bit removably couplable to the drill head and having a hollow coring head configured to separate a core from a tissue sample and retain the core therein, the drill bit having a central passageway fluidly coupling the hollow coring head to a port extending radially from the central passageway through the drill bit;
   a tube positioned radially outward from the drill bit and aligned with the port, wherein the tube is movable to selectively abut the drill bit to create a fluid seal between the tube and the port; and
   a pump fluidly coupled to the tube to cause a fluid to flow through the tube and pressurize the central passageway to eject the core.

2. The tissue sample core extractor of example 1, further comprising an outer body positioned at least partially around the drill head, the drill bit, the tube, and the pump, wherein the outer body includes a handle configured to be grasped by a hand of a user.

3. The tissue sample core extractor of examples 1 or 2, further comprising a trigger protruding from the outer body and movable to depress an actuator configured to cycle the pump and cause the fluid to flow through the tube.

4. The tissue sample core extractor of example 3 wherein the trigger is movable through (a) a first stage defined by a movement of the trigger causing the tube to abut the drill bit and create the fluid seal between the tube and the port, and (b) a second stage defined by a movement of the trigger causing the actuator to cycle the pump.

5. The tissue sample core extractor of any of examples 3 and 4 wherein:
   the trigger further comprises a first pin configured to travel in a first slot and a second pin configured to travel in a second slot,
   the first slot has a linear portion corresponding to the first stage of the trigger and an arcuate portion corresponding to the second stage of the trigger, and the second slot is linear.

6. The tissue sample core extractor of any of examples 3-5 wherein:
   movement of the trigger through the first stage pulls a cable coupling the trigger to a first jaw carrying an end of the tube adjacent to the drill bit, and
   movement of the trigger through the second stage elongates a spring positioned between the trigger and the first jaw, such that the movement of the trigger through the second stage does not cause further movement of the first jaw.

7. The tissue sample core extractor of any of examples 1-6 wherein the drill bit further comprises a second port extending radially from the central passageway through the drill bit opposite the port.

8. The tissue sample core extractor of any of examples 3-7, further comprising a blind tube positioned diametrically opposed to the tube and carried by a second jaw, wherein movement of the trigger through the first stage causes the first jaw and second jaw to move toward the drill bit and create a fluid seal around the drill bit such that at least one of the ports of the drill bit is in fluid communication with the tube at any rotational position of the drill bit.

9. The tissue sample core extractor of any of examples 1-8 wherein the fluid is a buffered liquid or a compressed gas.

10. The tissue sample core extractor of any of examples 1-9, further comprising a fluid container having a plunger to supply the fluid to the tube.

11. The tissue sample core extractor of any of examples 1-10, further comprising a chamber fluidly coupled to the pump, the fluid container, and the tube, the chamber configured to retain a portion of the fluid from the fluid container and pressurize by cycling of the pump.

12. The tissue sample core extractor of any of examples 1-11 wherein the drill bit has a shoulder positioned near the coring head and configured to prevent the coring head from entering the tissue sample further than depth of the shoulder.

13. A device for extracting a tissue sample core, comprising:
   an outer body;
   a drill head positioned within the outer body and rotatable by a motor;
   a drill bit extending from the outer body and removably couplable to the drill head, the drill bit having a hollow coring head configured to separate a core from a tissue sample and retain the core therein, the drill bit having a central passageway fluidly coupling the hollow coring head to a first port extending radially from the central passageway through the drill bit;
   a tube having an end positioned radially outward from the drill bit and aligned with the port, wherein the tube is movable by a trigger slidably associated with the outer body from (a) a first position at which the end of the tube is spaced apart from the drill bit, to (b) a second position at which the end of the tube abuts the drill bit to create a fluid seal between the tube and the first port; and
   a pump fluidly coupled to the tube to cause a fluid to flow through the tube in the second position and pressurize the central passageway to eject the core.

14. The device of example 13 wherein the outer body further comprises a handle configured to be grasped by a hand of a user.

15. The device of examples 13 or 14 wherein the trigger is rotatably associated with the outer body from the second position to a third position, and wherein rotation of the trigger to the third position depresses an actuator configured to cycle the pump and cause the fluid to flow through the tube.

16. The device of any of examples 13-15 wherein the trigger comprises a first stage and a subsequent second stage, the first stage defined by sliding movement of the trigger causing the end of the tube to abut the drill bit and create the fluid seal between the tube and the first port, and wherein the second stage is defined by rotational movement of the trigger causing the actuator to cycle the pump.

17. The device of any of examples 13-16 wherein:
   the trigger further comprises a first pin configured to travel in a first slot of the outer body and a second pin configured to travel in a second slot of the outer body,
   the first slot has a linear portion corresponding to the first stage of the trigger and an arcuate portion corresponding to the second stage of the trigger, and

the second slot is linear.

18. The device of any of examples 13-17 wherein:
   movement of the trigger through the first stage pulls a cable that couples the trigger to a first jaw carrying the end of the tube, and
   movement of the trigger through the second stage elongates a spring positioned between the trigger and the first jaw, such that the movement of the trigger through the second stage does not cause further movement of the first jaw.

19. The device of any of examples 13-18 wherein the drill bit further comprises a second port extending radially from the central passageway through the drill bit opposite the first port.

20. The device of any of examples 13-19, further comprising a blind tube positioned diametrically opposed to the tube and carried by a second jaw, wherein the movement of the trigger through the first stage causes the first jaw and second jaw to move toward the drill bit and create a fluid seal around the drill bit such that at least one of the first and second ports of the drill bit is in fluid communication with the tube at any rotational position of the drill bit.

21. The device of any of examples 13-20 wherein the fluid is a buffered liquid or a compressed gas.

22. The device of any of examples 13-21, further comprising:
   a fluid container having a plunger to supply the fluid to the tube; and/or
   a barcode reader configured to receive identifying information related to the tissue sample.

23. The device of any of examples 13-22, further comprising a chamber fluidly coupled to the pump, the fluid container, and the tube, the chamber configured to retain a portion of the fluid from the fluid container and pressurize by cycling of the pump.

24. The device of any of examples 13-23 wherein the drill bit has a shoulder positioned near the coring head and configured to prevent the coring head from entering the tissue sample further than depth of the shoulder.

D. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

For ease of reference, identical reference numbers are used to identify similar or analogous components or features throughout this disclosure, but the use of the same reference number does not imply that the features should be construed to be identical. Indeed, in many examples described herein, identically numbered features have a plurality of embodiments that are distinct in structure and/or function from each other. Furthermore, the same shading may be used to indicate materials in cross section that can be compositionally similar, but the use of the same shading does not imply that the materials should be construed to be identical unless specifically noted herein.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. As used herein, with respect to measurements, "about" means +/–5%. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A tissue sample core extractor, comprising:
a drill head configured to be rotated by a motor;
a drill bit removably couplable to the drill head and having a hollow coring head configured to separate a core from a tissue sample and retain the core therein, the drill bit having a central passageway fluidly coupling the hollow coring head to a first port extending radially from the central passageway through the drill bit;
a tube positioned radially outward from the drill bit and aligned with the first port, wherein the tube is movable to selectively abut the drill bit to create a fluid seal between the tube and the first port;
a pump fluidly coupled to the tube to cause a fluid to flow through the tube and pressurize the central passageway to eject the core; and
a trigger protruding from an outer body and movable to depress an actuator configured to cycle the pump and cause the fluid to flow through the tube,
wherein the trigger is movable through (a) a first stage defined by a movement of the trigger causing the tube to abut the drill bit and create the fluid seal between the tube and the first port, and (b) a second stage defined by a movement of the trigger causing the actuator to cycle the pump.

2. The tissue sample core extractor of claim 1, wherein the outer body is positioned at least partially around the drill head, the drill bit, the tube, and the pump, wherein the outer body includes a handle configured to be grasped by a hand of a user.

3. The tissue sample core extractor of claim 1 wherein:
the trigger further comprises a first pin configured to travel in a first slot and a second pin configured to travel in a second slot,
the first slot has a linear portion corresponding to the first stage of the trigger and an arcuate portion corresponding to the second stage of the trigger, and
the second slot is linear.

4. The tissue sample core extractor of claim 1 wherein:
movement of the trigger through the first stage pulls a cable coupling the trigger to a first jaw carrying an end of the tube adjacent to the drill bit, and
movement of the trigger through the second stage elongates a spring positioned between the trigger and the first jaw, such that the movement of the trigger through the second stage does not cause further movement of the first jaw.

5. The tissue sample core extractor of claim 3, further comprising a blind duct positioned diametrically opposed to the tube and carried by a second jaw, wherein movement of the trigger through the first stage causes the first jaw and the second jaw to move toward the drill bit and create a fluid seal around the drill bit such that the first port for a second port extending radially from the central passageway through the drill bit opposite the first port of the drill bit is in fluid communication with the tube at any rotational position of the drill bit.

6. The tissue sample core extractor of claim 1 wherein the drill bit further comprises a second port extending radially from the central passageway through the drill bit opposite the first port.

7. The tissue sample core extractor of claim 1, further comprising a chamber fluidly coupled to the pump, a fluid container, and the tube, the chamber configured to retain a portion of the fluid from the fluid container and pressurize by cycling of the pump.

8. The tissue sample core extractor of claim 1 wherein the drill bit has a shoulder positioned near the coring head and configured to prevent the coring head from entering the tissue sample further than depth of the shoulder.

9. A device for extracting a tissue sample core, comprising:
an outer body;
a drill head positioned within the outer body and rotatable by a motor;
a drill bit extending from the outer body and removably couplable to the drill head, the drill bit having a hollow coring head configured to separate a core from a tissue sample and retain the core therein, the drill bit having a central passageway fluidly coupling the hollow coring head to a first port extending radially from the central passageway through the drill bit;
a tube having an end positioned radially outward from the drill bit and aligned with the first port, wherein the tube is movable by a trigger slidably associated with the outer body from (a) a first position at which the end of the tube is spaced apart from the drill bit, to (b) a second position at which the end of the tube abuts the drill bit to create a fluid seal between the tube and the first port; and
a pump fluidly coupled to the tube to cause a fluid to flow through the tube in the second position and pressurize the central passageway to eject the core.

10. The device of claim 9 wherein the trigger is rotatably associated with the outer body from the second position to a third position, and wherein rotation of the trigger to the third position depresses an actuator configured to cycle the pump and cause the fluid to flow through the tube.

11. The device of claim 9 wherein the trigger comprises a first stage and a second stage, the first stage defined by sliding movement of the trigger causing the end of the tube to abut the drill bit and create the fluid seal between the tube and the first port, and wherein the second stage is defined by rotational movement of the trigger causing the actuator to cycle the pump.

12. The device of claim 11 wherein:

the trigger further comprises a first pin configured to travel in a first slot of the outer body and a second pin configured to travel in a second slot of the outer body, the first slot has a linear portion corresponding to the first stage of the trigger and an arcuate portion corresponding to the second stage of the trigger, and the second slot is linear.

13. The device of claim 11 wherein:

movement of the trigger through the first stage pulls a cable that couples the trigger to a first jaw carrying the end of the tube, and movement of the trigger through the second stage elongates a spring positioned between the trigger and the first jaw, such that the movement of the trigger through the second stage does not cause further movement of the first jaw.

14. The device of claim 13, further comprising a blind duct positioned diametrically opposed to the tube and carried by a second jaw, wherein the movement of the trigger through the first stage causes the first jaw and the second jaw to move toward the drill bit and create a fluid seal around the drill bit such that the first port or a second port extending radially from the central passageway through the drill bit opposite the first port of the drill bit is in fluid communication with the tube at any rotational position of the drill bit.

15. The device of claim 9 wherein the drill bit further comprises a second port extending radially from the central passageway through the drill bit opposite the first port.

16. The device of claim 9 wherein the fluid is a buffered liquid or a compressed gas.

17. The device of claim 9, further comprising:

a fluid container having a plunger to supply the fluid to the tube; and/or a barcode reader configured to receive identifying information related to the tissue sample.

18. The device of claim 9, further comprising a chamber fluidly coupled to the pump, a fluid container having a plunger to supply the fluid to the tube, and the tube, the chamber configured to retain a portion of the fluid from the fluid container and pressurize by cycling of the pump.

* * * * *